US012734167B2

(12) United States Patent
Patel et al.

(10) Patent No.: US 12,734,167 B2
(45) Date of Patent: Sep. 15, 2026

(54) NALTREXONE FORMULATION

(71) Applicant: INTAS PHARMACEUTICALS LTD., Ahmedabad (IN)

(72) Inventors: Alkeshkumar Narayanbhai Patel, Sanand Gujarat (IN); Manish Mavjibhai Patel, Sanand Gujarat (IN); Manishkumar Jayantibhai Chauhan, Sanand Gujarat (IN); Venkataramana Naidu, Sanand Gujarat (IN)

(73) Assignee: Intas Pharmaceuticals Ltd., Ahmedabad (IN)

( * ) Notice: Subject to any disclaimer, the term of this patent is extended or adjusted under 35 U.S.C. 154(b) by 998 days.

(21) Appl. No.: 17/625,478

(22) PCT Filed: Jul. 7, 2020

(86) PCT No.: PCT/IB2020/056364
§ 371 (c)(1),
(2) Date: Jan. 7, 2022

(87) PCT Pub. No.: WO2021/005501
PCT Pub. Date: Jan. 14, 2021

(65) Prior Publication Data

US 2022/0273645 A1 Sep. 1, 2022

(30) Foreign Application Priority Data

Jul. 10, 2019 (IN) ............................ 201921027547

(51) Int. Cl.
*A61K 31/485* (2006.01)
*A61K 9/00* (2006.01)

(52) U.S. Cl.
CPC .......... *A61K 31/485* (2013.01); *A61K 9/0056* (2013.01)

(58) Field of Classification Search
CPC ............................ A61K 31/485; A61K 9/0056
See application file for complete search history.

(56) References Cited

U.S. PATENT DOCUMENTS

| | | | | |
|---|---|---|---|---|
| 3,332,950 A | 7/1967 | Blumberg et al. | | |
| 6,194,382 B1 | 2/2001 | Crain et al. | | |
| 7,879,870 B2 | 2/2011 | Smith et al. | | |
| 2003/0191147 A1* | 10/2003 | Sherman | ................ | A61K 9/485 514/282 |

FOREIGN PATENT DOCUMENTS

| | | | | |
|---|---|---|---|---|
| EP | 2289492 A2 | 3/2011 | | |
| EP | 3130338 A1 | 2/2017 | | |
| WO | 0185257 A2 | 11/2001 | | |
| WO | 11085181 A1 | 7/2011 | | |
| WO | WO-2011085181 A1 * | 7/2011 | ............ | A61K 31/35 |
| WO | 16125108 A1 | 8/2016 | | |
| WO | 17141104 A2 | 8/2017 | | |

OTHER PUBLICATIONS

Song et al., "Variable efficacy of radical scavengers and iron chelators to attenuate gentamicin ototoxicity in guinea pig in vivo", 1996, Hearing Research, 94, pp. 87-93 (Year: 1996).*

Saigal et al., "Microcrystalline Cellulose as a Versatile Excipient in Drug Research", 2009, J Young Pharm, 1, pp. 6-12 (Year: 2009).*

International Search Report for PCT/IB2020/056364, Prepared by the European Patent Office, Mailing date Oct. 27, 2020, 6 pages.

Christian V. Tirpitz et al.: "Lactose intolerance in Crohn's disease patients: Comparison of clinical features with the expression and the activity of b-galactosidase in the intestinal mucosa", American Gastroenterological Association, vol. 118, No. 4, Apr. 2000 (Apr. 1, 2000), pp. A317.

Jill P. Smith et al.: "Safety and tolerability of low dose naltrexone therapy in children with moderate to severe crohn's disease: a pilot study", Journal of Clinical Gastroenterology, vol. 47, No. 4, Apr. 2013 (Apr. 1, 2013), pp. 339-345.

Tawfik Dina Ibrahim et al: "Evaluation of therapeutic effect of low dose naltrexone in experimentally-induced Crohn's disease in rats", Neuropeptides, Churchill Livingstone, GB, vol. 59, Jun. 22, 2016 (Jun. 22, 2016), pp. 39-45.

* cited by examiner

*Primary Examiner* — Brenda L Coleman
*Assistant Examiner* — Madeline E Braun
(74) *Attorney, Agent, or Firm* — BROOKS KUSHMAN P.C.

(57) ABSTRACT

A lactose free, stable pharmaceutical composition having naltrexone or its pharmaceutically acceptable salt thereof. Also disclosed is a process for the preparation of the composition and its use in a method for the treatment of Crohn's disease.

4 Claims, No Drawings

NALTREXONE FORMULATION

CROSS-REFERENCE TO RELATED APPLICATION

This application is the U.S. national phase of PCT Application No. PCT/IB2020/056364 filed on Jul. 7, 2020, which is related to Indian Provisional Application No. IN201921027547 filed on Jul. 10, 2019 the disclosures of which are incorporated in their entirety by reference herein.

FIELD OF THE INVENTION

The present invention related to lactose free, stable pharmaceutical composition comprising naltrexone or its pharmaceutically acceptable salt thereof. Further, the present invention provides process for the preparation of the said composition and its use for the treatment of Crohn's disease.

BACKGROUND OF THE INVENTION

Naltrexone is an opioid antagonist, is a synthetic congener of oxymorphone with no opioid agonist properties which is chemically known (4R,4aS,7aR,12bS)-3-(cyclopropylmethyl)-4a,9-dihydroxy-2,4,5,6,7a,13-hexahydro-1H-4,12-methano benzofuro[3,2-e]isoquinoline-7-one or morphinan-6-one, 17 (cyclopropylmethyl) 4,5-epoxy3,14-dihydroxy-(5∝) and molecular formula is $C_{20}H_{23}NO_4$.

FIG. 1

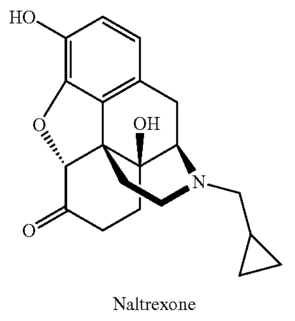

Naltrexone

Naltrexone is commercially available in tablet form (Revia®) and extended-release injectable suspension form (Vivitrol®) for the treatment of alcohol dependence and opioid dependence.

U.S. Pat. No. 3,332,950 patent covers naltrexone as compound and method for synthesis of naltrexone. When coadministered with morphine, heroin or other opioids on a chronic basis in a sufficient amount, naltrexone may reduce the incidence of physical dependence to opioids.

WO0185257 discloses solid oral dosage form comprising an opioid antagonist such as naltrexone in an amount of at least about 0.0001 mg to about or less than about 1.0 mg and further, comprising a stabilizer and one or more pharmaceutically acceptable carrier.

EP2289492 patent discloses pharmaceutical composition comprising naltrexone hydrochloride in amount of 20 mg or less, and further comprising a stabilizer and a chelating agent for inhibiting the formation of degradation product of the naltrexone hydrochloride.

In a normal course of therapy, Naltrexone is prescribed at a daily dose of 50 mg for the treatment of alcohol and opioid dependence. Further, there are several clinical studies have been shown that low dose naltrexone (LDN) improves clinical and inflammatory activity of subjects with moderate to severe Crohn's disease compared to placebo-treated controls.

LDN is a term for using naltrexone at a much lower dose than normally prescribed. LDN was used as sole therapy in children with moderate-to-severe Crohn's disease and it is well tolerated without any serious adverse events in children with moderate to severe Crohn's disease (see Jill P. Smith, et al. *Safety and tolerability of low dose naltrexone therapy in children with moderate to severe crohn's disease: a pilot study. Journal of Clinical Gastroenterology.* 2013 April; 47(4): 339-345).

U.S. Pat. No. 6,194,382 patent describes a method for treating irritable bowel syndrome comprising administering at a dose between about 0.1 mg/day and about 5 mg/day of an excitatory opioid receptor antagonist such as naltrexone.

U.S. Pat. No. 7,879,870 patent discloses a method for treating Crohn's disease comprising a therapeutically effective dose less than 50 mg of an opioid antagonist like naltrexone, wherein the therapeutically effective dose of less than 50 mg is from about 1.75 mg to about 4.5 mg of opioid antagonist. Further, this patent also discloses that low dose naltrexone is safe, effective and has advantages over other standard therapy for the treatment of Crohn's disease.

However, lactose intolerance is a frequent problem in Crohn's disease patients, leading to increased diarrhoea, bloating and abdominal pain. Consecutive avoidance of milk products is a risk for calcium deficiency possibly leading to pathological bone mineralisation and increased risk of bone fractures. (see Christian v. Tirpitz, et al., *Lactose intolerance in Crohn's disease patients: Comparison of clinical features with the expression and the activity of b-galactosidase in the intestinal mucosa., American Gastroenterological Association*, April 2000: Volume 118, Issue 4, Part 1, Page A317).

From the prior art, it can be inferred that there are issues with the use of lactose with naltrexone which may produce diarrhea, bloating and abdominal pain. The present invention addresses the need to provide a lactose free and stable pharmaceutical composition comprising naltrexone to overcome the above-mentioned problems.

The inventors of the present invention have found lactose free, stable pharmaceutical composition comprising naltrexone or its pharmaceutically acceptable salt thereof. Furthermore, the present invention is also devoid of any stabilizers and chelating agent.

In addition, the present invention provides process for the preparation of the said composition, and the use of the said pharmaceutical composition for the treatment of Crohn's disease.

OBJECT OF THE INVENTION

The first object of the present invention is to provide lactose free, stable pharmaceutical composition comprising naltrexone or its pharmaceutically acceptable salt thereof.

Another object of the present invention is to provide lactose free, stable pharmaceutical composition comprising naltrexone or its pharmaceutically acceptable salt thereof, wherein the said composition is devoid of any stabilizer or chelating agent.

Another object of the present invention is to provide lactose free, stable pharmaceutical composition comprising naltrexone or its pharmaceutically acceptable salt thereof, wherein the therapeutically effective dose of naltrexone in the said composition is less than 10 mg.

Another object of the present invention is to provide lactose free, stable pharmaceutical composition comprising naltrexone or its pharmaceutically acceptable salt thereof, wherein the therapeutically effective dose of naltrexone in the said composition is less than 10 mg, and is used for the treatment of Crohn's disease.

Another object of the present invention is to provide lactose free, stable pharmaceutical composition comprising naltrexone or its pharmaceutically acceptable salt thereof, wherein the therapeutically effective dose of naltrexone in the said composition is less than 10 mg, and is used for the treatment of Crohn's disease in pediatric patients.

Another object of the present invention is to provide lactose free, stable pharmaceutical composition comprising naltrexone or its pharmaceutically acceptable salt thereof, wherein the therapeutically effective dose of naltrexone in the said composition is from about 1.5 mg to about 5 mg, and is used for the treatment of Crohn's disease.

Another object of the present invention is to provide lactose free, stable pharmaceutical composition comprising naltrexone or its pharmaceutically acceptable salt thereof, wherein the therapeutically effective dose of naltrexone in the said composition is from about 1.5 mg to about 5 mg, and is used for the treatment of Crohn's disease in pediatric patients.

Another object of the present invention is to provide lactose free, stable pharmaceutical composition comprising naltrexone or its pharmaceutically acceptable salt thereof, and one or more pharmaceutically acceptable excipients.

Another object of the present invention is to provide lactose free, stable pharmaceutical composition comprising naltrexone or its pharmaceutically acceptable salt thereof and one or more pharmaceutically acceptable excipients selected from one or more fillers, one or more diluents, one or more disintegrants, one or more binders, one or more glidants, one or more lubricants, one or more surfactants or the mixtures thereof.

Another object of the present invention is to provide lactose free, stable pharmaceutical composition comprising naltrexone or its pharmaceutically acceptable salt thereof, wherein the said composition is in the form of dispersible tablets.

In another embodiment, the present invention is to provide lactose free, stable pharmaceutical composition comprising naltrexone or its pharmaceutically acceptable salt thereof, wherein the said composition is in the form of dispersible tablets and the disintegration time of the said dispersible tablets is less than 10 minutes when dispersed in water.

Another object of the present invention is to provide process for preparation of lactose free, stable pharmaceutical composition comprising naltrexone or its pharmaceutically acceptable salt thereof and one or more pharmaceutical acceptable excipients.

Another object of the present invention is to provide lactose free, stable pharmaceutical composition comprising naltrexone or its pharmaceutically acceptable salt thereof and one or more pharmaceutically acceptable excipients, wherein the content uniformity of the said composition is in between 95% and 105%.

Another object of the present invention is to provide lactose free, stable pharmaceutical composition comprising naltrexone or its pharmaceutically acceptable salt thereof and one or more pharmaceutically acceptable excipients, wherein the dissolution rate of naltrexone is not less than 90% at 45 minutes when the composition is subjected to the dissolution test using paddle method at a rotation of 50 rpm in 900 ml of purified water.

Another object of the present invention is to provide lactose free, stable pharmaceutical composition comprising naltrexone or its pharmaceutically acceptable salt thereof and one or more pharmaceutically acceptable excipients, wherein the said composition does not have more than 3% (w/w) of total impurity, more preferably does not have more than 1% of total impurity after being stored at specific storage conditions.

Another object of the present invention is to provide lactose free, stable pharmaceutical composition comprising naltrexone or its pharmaceutically acceptable salt thereof and one or more pharmaceutical acceptable excipients, wherein the said composition does not have more than 0.4% (w/w) of unknown impurity of naltrexone after being stored at specific storage conditions.

SUMMARY OF THE INVENTION

The present invention related to lactose free, stable pharmaceutical composition comprising naltrexone or its pharmaceutically acceptable salt thereof. Further the present invention provides process for the preparation of the said composition and its use for the treatment of Crohn's diseases, wherein the therapeutically effective dose of naltrexone in the said composition is less than 10 mg.

DETAILED DESCRIPTION

Unless otherwise indicated, terms in this specification are intended to have their ordinary meaning in the relevant art.

The present invention related to lactose free, stable pharmaceutical composition comprising naltrexone or its pharmaceutically acceptable salt thereof. Further, the present invention provides process for the preparation of the said composition and its use for the treatment of Crohn's disease.

The term "Naltrexone" used throughout the specification refers to not only their base per se, but also their other pharmaceutically acceptable salt, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof.

The term "pharmaceutically acceptable" means salt, carriers, excipients, and other formulation ingredients that are compatible with all other pharmaceutical ingredients of a composition and are not deleterious to an individual treated with composition.

The term "stabilizer" used throughout the specification refers to any chemical or agents inhibit the degradation of naltrexone hydrochloride by inhibiting the formation of a degradation product. The said stabilizer includes for example and without limitation, organic acids, carboxylic acids, acid salts of amino acids (e.g., cysteine, L-cysteine, cysteine hydrochloride, glycine hydrochloride or cystine dihydrochloride), sodium metabisulphite, ascorbic acid and its derivatives, malic acid, isoascorbic acid, citric acid, tartaric acid, sodium carbonate, sodium hydrogen carbonate, calcium carbonate, calcium hydrogen phosphate, sulphur dioxide, sodium sulphite, sodium bisulphate, tocopherol, as well as its water- and fat-soluble derivatives, such as e.g., tocofersolan or tocopherol acetate, sulphites, bisulphites and hydrogen sulphites or alkali metal, alkaline earth metal and other metals, PHB esters, gallates, butylated hydroxyanisol (BHA) or butylated hydroxytoluene (BHT), and 2,6-di-t-butyl-alpha-dimethylamino-p-cresol, t-butylhydroquinone, di-t-amylhydroquinone, di-t-butylhydroquinone, butylhydroxytoluene, butylhydroxyanisole, pyrocatechol, pyrogallol, propylgallate, and nordihydroguaiaretic acid, as well as lower fatty acids, fruit acids, phosphoric acids, sorbic and benzoic acids as well as their salts, esters, derivatives and isomeric compounds, ascorbyl palmitate, lecithins, mono- and polyhydroxylated benzene derivatives, ethylenediamine-tetraacetic acid and its salts, citraconic acid, conidendrine, diethyl carbonate, methylenedioxyphenols, kephalines, β,β'-dithiopropionic acid, biphenyl and other phenyl derivatives, pharmaceutically acceptable salts thereof, and mixtures thereof.

The "chelating agent" used throughout the specification refers to any chemical compound which forms a complex with metal ion that catalyzes the degradation of naltrexone hydrochloride through oxidation and hydrolytic reactions. Therefore, chelating agents are used in inhibiting the degradation of naltrexone hydrochloride. The said "chelating agent" includes for example and without limitation, EDTA (ethylenediamine-tetraacetic acid), a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), 2-(2-amino-2-oxocthyl) aminoethane sulfonic acid (BES), diethylenetriaminepentaacetic acid, bis(aminoethyl)glycolether-N,N,N',N'-tetraacetic acid, N-2-acetamido-2-iminodiacetic acid (ADA), N-hydroxyethyliminodiacetic acid (HIMDA), N,N-bis-hydroxyethylglycine (bicine), N-(trishydroxymethylmethyl)glycine (tricine), glycylglycine, iminodiacetic acid, citric acid, tartaric acid, fumaric acid, glutamic acid, aspartic acid mixtures thereof, and salts thereof.

A "therapeutically effective dose" is an amount sufficient to effect desired clinical results (i.e., achieve therapeutic efficacy). A therapeutically effective dose can be administered in one or more administrations. For purposes of this invention, a therapeutically effective dose of naltrexone is an amount that is sufficient to palliate, ameliorate, stabilize, reverse, prevent, slow or delay the progression of the disease state (i.e. Crohn's disease).

The term "content uniformity" means the homogeneity of the naltrexone content among dosage forms after formulation. Content uniformity and acceptance value test can be performed according to revised US Pharmacopoeia chapter <905> Uniformity of dosage units. The term of "Uniformity of dosage unit" is defined as the degree of uniformity in the amount of drug substance among dosage units. According to US pharmacopoeia criteria, the requirements for dosage uniformity is met if the acceptance value of the first 10 dosage unit is less than or equal to 15%.

The term "stable" as used throughout the specification, refers to a pharmaceutical composition in which the active pharmaceutical ingredients naltrexone is present in an amount of at least 90% of the original label specified amount for each such ingredient during specific storage conditions.

The term "specific storage conditions" as used throughout the specification, refers to the pharmaceutical composition of present invention stored for at least 6 months at 40° C./75% RH and 25° C./60% RH.

The term "total impurities" of naltrexone as used throughout the specification, refers to identified or unidentified degradation product or impurity structurally related with naltrexone which are arising from a manufacturing process or during storage of material. According to the present invention, the said pharmaceutical composition does not have more than 3% (w/w) of total impurity, more preferably does not have more than 1% of total impurity of naltrexone after being stored at specific storage conditions.

The identified impurities of Naltrexone are as follows:

Impurity D: 2,2'-Bisnaltrexone

Impurity F: 17-(Cyclopropylmethyl)-4,5α-epoxy-3,10α,14-trihydroxymorphinan-6-one Impurity G: 17-(Cyclopropylmethyl)-4,5α-epoxy-3,10β,14-trihydroxymorphinan-6-one Impurity I: 17-(Cyclopropylmethyl)-4,5α-epoxy-3,14-dihydroxymorphinan-6,10-dione Impurity H: N-Butyl Noroxymorphone In one of the embodiment, the present invention provides lactose free, stable pharmaceutical composition comprising naltrexone or its pharmaceutically acceptable salt thereof.

In one of another embodiment, the present invention provides lactose free, stable pharmaceutical composition comprising naltrexone or its pharmaceutically acceptable salt thereof, wherein the present composition is substantially free from lactose.

The term "substantially free" means the composition comprises less than about 1%, more preferably less than about 0.5%, most preferably less than about 0.1% of lactose by total weight of the composition.

In another embodiment, the present invention provides lactose free, stable pharmaceutical composition comprising naltrexone or its pharmaceutically acceptable salt thereof, wherein the said composition is devoid of any stabilizer or chelating agent.

In yet another embodiment, the present invention is to provide lactose free, stable pharmaceutical composition comprising naltrexone or its pharmaceutically acceptable salt thereof, wherein the therapeutically effective dose of naltrexone in the said composition is less than 10 mg.

The present invention is to provide lactose free, stable pharmaceutical composition comprising naltrexone or it's pharmaceutically acceptable salt thereof, wherein the therapeutically effective dose of naltrexone in the said composition is less than 10 mg, preferably less than 8 mg, more preferably less than 6 mg, most preferably is from about 1.5 mg to about 5 mg.

For the present invention, the term "about" shall mean a variation up to 10% (plus or minus 10%) of the particular term.

In yet another embodiment, the present invention is to provide lactose free, stable pharmaceutical composition comprising naltrexone or its pharmaceutically acceptable salt thereof, wherein the therapeutically effective dose of naltrexone in the said composition is less than 10 mg, and is used for the treatment of Crohn's disease.

In yet another embodiment, the present invention is to provide lactose free, stable pharmaceutical composition comprising naltrexone or its pharmaceutically acceptable salt thereof, wherein the therapeutically effective dose of naltrexone in the said composition is less than 10 mg, and is used for the treatment of Crohn's disease in pediatric patients.

In yet another embodiment, the present invention is to provide lactose free, stable pharmaceutical composition comprising naltrexone or its pharmaceutically acceptable salt thereof, wherein the therapeutically effective dose of naltrexone in the said composition is from about 1.5 mg to about 5 mg, and is used for the treatment of Crohn's disease.

In yet another embodiment, the present invention is to provide lactose free, stable pharmaceutical composition comprising naltrexone or its pharmaceutically acceptable salt thereof, wherein the therapeutically effective dose of naltrexone in the said composition is from about 1.5 mg to about 5 mg, and is used for the treatment of Crohn's disease in pediatric patients.

In another embodiment, the present invention is to provide lactose free, stable pharmaceutical composition comprising naltrexone or its pharmaceutically acceptable salt thereof, wherein the said composition is in the form of dispersible tablets.

In another embodiment, the present invention is to provide lactose free, stable pharmaceutical composition comprising naltrexone or its pharmaceutically acceptable salt thereof, wherein the said composition is in the form of dispersible tablets and the disintegration time of the said dispersible tablets is less than 10 minutes when dispersed in water.

In one of the preferred embodiment, the present invention is to provide lactose free, stable pharmaceutical composition comprising naltrexone or its pharmaceutically acceptable salt thereof and one or more pharmaceutical acceptable excipients.

In yet another embodiment, the present invention is to provide lactose free, stable pharmaceutical composition comprising naltrexone or its pharmaceutically acceptable salt thereof and one or more pharmaceutical acceptable excipients selected from one or more fillers, one or more diluents, one or more disintegrants, one or more binders, one or more glidants, one or more lubricants, one or more surfactants or the mixtures thereof. The amount of each excipient in a solid dosage formulation may vary within ranges conventional in the art.

The fillers or diluents can be selected from the group comprising of but not limited to mannitol, dibasic calcium phosphate anhydrous, microcrystalline cellulose, corn starch, sucrose or other sugar or sugar derivatives, low substituted HPC, pregelatinized starch or mixture thereof, more preferably mannitol and microcrystalline cellulose. The fillers or diluents can be present in a concentration of from about 20% to about 80% by weight of the total weight of the composition. Mannitol may perform dual properties such as a filler or diluent and can also act as a taste-masking agent and can provide cooling-effect.

The disintegrant can be selected from the group comprising of but not limited to croscarmellose sodium, crospovidone, sodium starch glycolate, starch, corn starch, pregelatinized starch or mixture thereof. The disintegrant can be present in a concentration of from about 1% to about 10% by weight of the total weight of the composition.

The binder can be selected from the group comprising of but not limited to pregelatinized starch, polyvinylpyrrolidone, povidone, copovidone, hydroxypropyl methyl cellulose, hydroxypropyl cellulose, maize starch, microcrystalline cellulose or mixture thereof. The binder can be present in a concentration of from about 0.5% to about 5% by weight of the total weight of the composition.

The lubricant can be selected form the group comprising of agar, calcium stearate, ethyl oleate, ethyl laureate, glycerin, glyceryl palmitostearate, hydrogenated vegetable oil, magnesium oxide, magnesium stearate, sodium stearyl, sorbitol, stearic acid, talc, and zinc stearate or mixture thereof. The lubricant can be present in a concentration of from about 0.2% to about 2% by weight of the total weight of the composition.

The glidant can be selected from the group comprising of colloidal silicon dioxide, magnesium silicate, starch, talc, tribasic calcium phosphate, stearic acid, palmitic acid, polyethylene glycol, carnauba wax or mixtures thereof. The glidant can be present in a concentration of from about 0% to about 2% by weight of the total weight of the composition.

The surfactants can be selected from the group comprising of anionic surfactants such as sodium lauryl sulfate and docusate sodium, cationic surfactants such as cetrimide, ampholytic surfactants such as N-dodecyl-N, N-dimethylbetaine, non-ionic surfactants such as sorbitan fatty acid esters, polysorbates, polyoxyethylene alkyl ethers, poloxamers, medium-chain triglycerides, polyoxylglycerides, polyoxyethylene castor oil derivatives and combinations thereof. The surfactants can be present in a concentration of from about 0% to about 5% by weight of the total weight of the composition.

The film coating material is a polymeric film coating material comprising hydroxypropyl methylcellulose, polyethylene glycol, hydroxypropyl cellulose, polysorbate, sodium carboxy methyl cellulose, Talc, Titanium dioxide, simethicon, Eudragit, purified water and colorant. The film coating material can be present in a concentration of from about 1% to about 5% by weight of the total weight of the composition.

The colorant can be selected from the group comprising of but not limited Sunset yellow Lake, carmine, iron oxide yellow, iron oxide red, indigo carmine, orange yellow S, quinoline yellow, indigo tine lake, brilliant blue and/or mixture thereof.

The solvent can be selected from the group comprising of but not limited purified water, ethanol, isopropanol, acetone or mixture thereof. The solvent can be used during the granulation stage as a granulating fluid and/or during the coating stage as a coating solution.

The pharmaceutical composition described herein may be prepared by conventional technology well known to those skilled in the art such as wet granulation, dry granulation and direct compression and the like.

The present invention is to provide lactose free, stable pharmaceutical composition comprising naltrexone or its pharmaceutically acceptable salt thereof and one or more pharmaceutical acceptable excipients, wherein the said composition is in form of capsule, granules, reconstitutable powders, dry syrup, chewable tablet, powder, lozenges, or sachets.

In one of the preferred embodiment, present invention is to provide a process for preparation of a lactose free stable pharmaceutical composition comprising naltrexone or its pharmaceutically acceptable salt thereof and one or more pharmaceutical acceptable excipients comprising following steps.

1) Mixing naltrexone HCl with diluent and disintegrants to obtain a blend.
2) Disperse binder in solvent under stirring to obtain a binder solution.
3) Granulate the blend obtained in step 1 in a granulator with binder solution to obtain wet granules. Dry the wet granules.
4) Size the dried granules and add desired amount of lubricant to obtain lubricated granules.
5) Compress the lubricated granules of step 6 to obtain compressed tablets.
6) Optionally, coat the compressed tablets using coating solution.

In one of the preferred embodiment, present invention is to provide lactose free, stable pharmaceutical composition comprising naltrexone or its pharmaceutically acceptable salt thereof and one or more pharmaceutical acceptable excipients, wherein the content uniformity of the said composition is in between 95% and 105%.

In one of the preferred embodiment, present invention is to provide lactose free, stable pharmaceutical composition comprising naltrexone or its pharmaceutically acceptable salt thereof and one or more pharmaceutical acceptable excipients, wherein the dissolution rate of naltrexone is not less than 90% at 45 minutes when the composition is subjected to the dissolution test using paddle method at a rotation of 50 rpm in 900 ml of purified water.

In one of the preferred embodiment, the present invention is to provide lactose free, stable pharmaceutical composition comprising naltrexone or its pharmaceutically acceptable salt thereof and one or more pharmaceutically acceptable excipients, wherein the said composition does not have more than 3% (w/w) of total impurity, more preferably does not have more than 1% of total impurity of naltrexone after being stored at specific storage conditions.

In one of the preferred embodiment, the present invention is to provide lactose free, stable pharmaceutical composition comprising naltrexone or its pharmaceutically acceptable salt thereof and one or more pharmaceutical acceptable excipients, wherein the said composition does not have more than 0.4% (w/w) of unknown impurity of naltrexone after being stored at specific storage conditions.

EXAMPLE

The present invention has been described by way of example only. It is to be recognized that modifications falling within the scope and spirit of the claims, which would be obvious to a person skilled in the art based upon the disclosure herein, are also considered to be included within the scope of this invention. The scope of the invention is in no manner limited by the disclosed example.

Example 1

| Sr. No | Ingredients | % w/w |
|---|---|---|
| 1 | Naltrexone | 1-5 |
| 2 | Diluent | 20-80 |

-continued

| Sr. No | Ingredients | % w/w |
|---|---|---|
| 3 | Disintegrant | 1-10 |
| 4 | Binder | 0.5-5 |
| 5 | Lubricant | 0.2-2 |
| 6 | Glidant | 0-2 |
| 7 | Surfactant | 0-5 |
| 8 | Solvent | Qs |
| 9 | Film Coating material | 1-5 |
| | Weight of coated tablet | 100 |

Manufacturing Process:

1. Mix Naltrexone with diluent and disintegrants to obtain a blend.
2. Disperse binder in solvent under stirring.
3. Granulate the blend obtained in step 1 in granulator with binder solution.
4. Dry the wet granules in fluid bed dryer then size the dried granules.
5. Lubricate the sized granules with sifted lubricant.
6. Compress the granules into tablets and coat the compressed tablets using coating solution prepared using film coating material in solvent.

Example 2

| Sr. No | Ingredients | 1.5 mg/tablet | 3 mg/tablet | 4.5 mg/tablet |
|---|---|---|---|---|
| 1 | Naltrexone hydrochloride | 1.500 | 3.000 | 4.500 |
| 2 | Mannitol | 40.000 | 80.000 | 120.000 |
| 3 | Microcrystalline cellulose | 14.450 | 28.900 | 43.350 |
| 4 | Sodium starch glycolate | 3.000 | 6.000 | 9.000 |
| 5 | Hydroxypropyl cellulose | 0.750 | 1.500 | 2.250 |
| 6 | Isopropyl Alcohol | Qs | Qs | Qs |
| 7 | Magnesium stearate | 0.300 | 0.600 | 0.900 |
| | Weight of core tablet | 60.000 | 120.000 | 180.000 |
| | Coating | | | |
| 8 | Opadry YS-1-6378 G Pale yellow | 2.000 | 4.000 | 6.000 |
| 9 | Purified water | Qs | Qs | Qs |
| | Weight of coated tablet | 62.000 | 124.000 | 186.000 |

Manufacturing Process:

1. Mix naltrexone HCl, mannitol, microcrystalline cellulose and sodium starch glycolate.
2. Disperse hydroxypropyl cellulose in isopropyl alcohol under stirring.
3. Granulate the material in rapid mixer granulator with binder solution.
4. Dry the wet granules in fluid bed dryer then size the dried granules.
5. Lubricate the sized granules with magnesium stearate to obtain a blend.
6. Compress the lubricated granules into tablet and coat the compressed tablets using coating solution prepared using Opadry in purified water.

Content Uniformity

Content uniformity of naltrexone tablet was evaluated for 10 individual tablets of three different strength 1.5 mg, 3 mg & 4.5 mg as per revised US Pharmacopoeia chapter <905> Uniformity of dosage units and gave the following results I table 1.

TABLE 1

| Naltrexone Tablet | 1.5 mg/tablet | 3 mg/tablet | 4.5 mg/tablet |
|---|---|---|---|
| Content uniformity | 100% (98%-103%) | 98% (97%-100%) | 99% (98%-100%) |
| % RSD of 10 tablets | 1.49% | 1.10% | 0.80% |
| Acceptance value | 3.6 | 3.6 | 1.9 |

RSD: Relative Standard Deviation

The above data of naltrexone tablets show the data of content uniformity, % RSD and acceptance value indicative of better content uniformity and acceptance value.

Dissolution Study

The composition of example 2 was tested for dissolution study as per USP dissolution apparatus 2 (paddle) at 50 rpm using 900 ml in purified water, and gave the following results as Table 2.

TABLE 2

| | | Time (Min) | | | | | |
|---|---|---|---|---|---|---|---|
| Sr. No. | Strength | 5 | 10 | 15 | 20 | 30 | 45 |
| 1 | 1.5 mg | 56 | 79 | 88 | 91 | 95 | 96 |
| 2 | 3 mg | 70 | 83 | 87 | 90 | 91 | 93 |
| 3 | 4.5 mg | 65 | 81 | 85 | 87 | 89 | 91 |

The above dissolution study data comply with the dissolution testing requirements of immediate release solid oral dosage forms.

Stability Study

TABLE 3

Stability data of naltrexone HCl tablets 1.5 mg under different time interval at condition of 40° C./75% RH and 25° C./60% RH in HDPE bottle.

| | | 40° C./75% RH | | 25° C./60% RH | |
|---|---|---|---|---|---|
| Test | Limit | 3 Month | 6 Month | 3 Month | 6 Month |
| Assay | 95-105 | 100.30% | 99.2% | 100.20% | 100.4% |
| Related substance | | | | | |
| Impurity D | NMT 1.0% | 0.018 | 0.027 | 0.007 | 0.016 |
| Impurity F | NMT 1.0% | ND | 0.104 | ND | 0.060 |
| Impurity G | NMT 1.0% | 0.017 | 0.035 | 0.009 | 0.012 |
| Impurity I | NMT 1.0% | 0.153 | 0.156 | 0.093 | 0.084 |
| Impurity H | NMT 1.0% | 0.07 | 0.064 | 0.029 | 0.040 |
| Single Max unknown | NMT 0.4% | 0.099 | 0.150 | 0.043 | 0.035 |
| Total impurity | NMT 3% | 0.679 | 0.763 | 0.27 | 0.370 |

ND: Not detected

The above data shows a total impurity not more than 1% in the formulation, indicative of stability of naltrexone HCl in the drug product.

TABLE 4

Stability data of naltrexone HCl tablets 1.5 mg under different time interval at condition of 40° C./75% RH and 25° C./60% RH in Alu-Alu Blister.

| | | 40° C./75% RH | | 25° C./60% RH | |
|---|---|---|---|---|---|
| Test | Limit | 3 Month | 6 Month | 3 Month | 6 Month |
| Assay | 95-105 | 99.40% | 99.6% | 100% | 100.3% |
| Related Substance | | | | | |
| Impurity D | NMT 1.0% | 0.017 | 0.022 | 0.018 | 0.016 |
| Impurity F | NMT 1.0% | ND | 0.114 | ND | 0.060 |
| Impurity G | NMT 1.0% | 0.016 | 0.023 | 0.009 | 0.012 |
| Impurity I | NMT 1.0% | 0.147 | 0.176 | 0.097 | 0.076 |

TABLE 4-continued

Stability data of naltrexone HCl tablets 1.5 mg under different time interval at condition of 40° C./75% RH and 25° C./60% RH in Alu-Alu Blister.

| | | 40° C./75% RH | | 25° C./60% RH | |
|---|---|---|---|---|---|
| Test | Limit | 3 Month | 6 Month | 3 Month | 6 Month |
| Impurity H | NMT 1.0% | 0.06 | 0.077 | 0.031 | 0.037 |
| Single Max unknown | NMT 0.4% | 0.091 | 0.094 | 0.046 | 0.039 |
| Total impurity | NMT 3% | 0.596 | 0.713 | 0.295 | 0.369 |

The above data shows a total impurity not more than 1% in the formulation, indicative of stability of naltrexone HCl in the drug product.

TABLE 5

Stability data of naltrexone HCl tablets 4.5 mg under different time interval at condition of 40° C./75% RH and 25° C./60% RH in HDPE bottle.

| | | 40° C./75% RH | | 25° C./60% RH | |
|---|---|---|---|---|---|
| Test | Limit | 3 Month | 6 Month | 3 Month | 6 Month |
| Assay | 95-105 | 99 | 98.9 | 98.45 | 99.2 |
| Related Substance | | | | | |
| Impurity D | NMT 1.0% | 0.016 | 0.022 | 0.015 | 0.014 |
| Impurity F | NMT 1.0% | ND | 0.102 | ND | 0.053 |
| Impurity G | NMT 1.0% | 0.014 | 0.020 | 0.008 | 0.010 |
| Impurity I | NMT 1.0% | 0.131 | 0.149 | 0.082 | 0.072 |
| Impurity H | NMT 1.0% | 0.057 | 0.067 | 0.021 | 0.034 |
| Single Max unknown | NMT 0.4% | 0.083 | 0.120 | 0.041 | 0.034 |
| Total impurity | NMT 3% | 0.515 | 0.635 | 0.242 | 0.326 |

The above data shows a total impurity not more than 1% in the formulation, indicative of stability of naltrexone HCl in the drug product.

TABLE 6

Stability data of naltrexone HCl tablets 4.5 mg under different time interval at condition of 40° C./75% RH and 25° C./60% RH in Alu Alu Blister.

| | | 40° C./75% RH | | 25° C./60% RH | |
|---|---|---|---|---|---|
| Test | Limit | 3 Month | 6 Month | 3 Month | 6 Month |
| Assay | 95-105 | 98.9 | 98.8 | 99 | 100.1 |
| Related Substance | | | | | |
| Impurity D | NMT 1.0% | 0.015 | 0.018 | 0.016 | 0.016 |
| Impurity F | NMT 1.0% | ND | 0.090 | ND | 0.052 |
| Impurity G | NMT 1.0% | 0.013 | 0.017 | 0.007 | 0.010 |
| Impurity I | NMT 1.0% | 0.121 | 0.141 | 0.084 | 0.061 |
| Impurity H | NMT 1.0% | 0.048 | 0.057 | 0.028 | 0.032 |
| Single Max unknown | NMT 0.4% | 0.075 | 0.072 | 0.041 | 0.037 |
| Total impurity | NMT 3% | 0.447 | 0.542 | 0.249 | 0.322 |

The above data shows a total impurity not more than 1% in the formulation, indicative of stability of naltrexone HCl in the drug product.

The stability data as mentioned above indicate that the lactose free pharmaceutical composition comprising naltrexone or its pharmaceutically acceptable salt thereof are stable.

We claim:

1. A lactose free, stable pharmaceutical composition comprising naltrexone or its pharmaceutically acceptable salt thereof and pharmaceutically acceptable excipients, wherein the amount of naltrexone or its pharmaceutically acceptable salt thereof in the pharmaceutical composition is from about 1.5 mg to about 5 mg, the content uniformity of the composition is in between 95% and 105%, wherein the pharmaceutical composition is in the form of a tablet, wherein the pharmaceutically acceptable excipients are:

mannitol and microcrystalline cellulose as diluents, present in an amount from about 20% w/w to about 80% w/w of the pharmaceutical composition;

sodium starch glycolate as disintegrant, present in an amount from about 1% w/w to about 10% w/w of the pharmaceutical composition;

hydroxypropyl cellulose as binder, present in an amount from about 0.5% w/w to about 5% w/w of the pharmaceutical composition; and magnesium stearate as lubricant, present in an amount from about 0.2% w/w to about 2% w/w of the pharmaceutical composition;

and wherein the pharmaceutical composition is devoid of any stabilizer or chelating agent.

2. The lactose free, stable pharmaceutical composition according to claim 1, wherein the pharmaceutical composition is formulated for oral administration in a dosage form suitable for the treatment of Crohn's disease.

3. The lactose free, stable pharmaceutical composition according to claim 1, wherein the composition does not have more than 3% (w/w) of total impurity when stored at 40° C./75% RH and 25° C./60% RH for at least 6 months.

4. The lactose free, stable pharmaceutical composition according to claim 1, wherein the composition exhibits a dissolution rate of naltrexone not less than 90% at 45 minutes when tested using a paddle dissolution apparatus 2 at a rotation speed of 50 rpm in 900 ml of purified water.

* * * * *